United States Patent [19]

Lang et al.

[11] Patent Number: 4,759,881

[45] Date of Patent: Jul. 26, 1988

[54] PROCESS FOR THE PREPARATION OF TRIFLUORODICHLOROETHYL-SUBSTITUTED ACIDS AND ZINC COMPOUNDS

[75] Inventors: Robert W. Lang, Pratteln, Switzerland; Bernd Klingert, Inzlingen, Fed. Rep. of Germany

[73] Assignee: Ciba-Geigy Corporation, Ardsley, N.Y.

[21] Appl. No.: 835,481

[22] Filed: Mar. 3, 1986

[30] Foreign Application Priority Data

Mar. 11, 1985 [CH] Switzerland ............ 1090/85

[51] Int. Cl.$^4$ .............. C07C 153/017; C07C 145/00; C07C 51/15

[52] U.S. Cl. .............. 260/502.6; 260/513.7; 562/551

[58] Field of Search ............ 260/513.7, 502.6; 562/551

[56] References Cited

U.S. PATENT DOCUMENTS

| | | | |
|---|---|---|---|
| 2,568,500 | 9/1951 | Husted et al. | 260/601 |
| 2,824,897 | 2/1958 | Wujciak et al. | 260/633 |
| 3,290,333 | 12/1966 | Fainberg | 556/122 |
| 3,732,274 | 5/1973 | Young et al. | 260/463 |

FOREIGN PATENT DOCUMENTS

| | | |
|---|---|---|
| 73569 | 3/1983 | European Pat. Off. . |
| 157739 | 10/1985 | European Pat. Off. . |
| 187674 | 7/1986 | European Pat. Off. . |
| 1816282 | 7/1969 | Fed. Rep. of Germany . |
| 2557162 | 7/1976 | Fed. Rep. of Germany . |
| 1496633 | 9/1967 | France . |
| 1122847 | 8/1968 | United Kingdom . |
| 1474867 | 5/1975 | United Kingdom . |

OTHER PUBLICATIONS

Posta et al., Collection Czechoslov. Chem. Commun., 37:3946–3949, (1972).
Blancou et al., J. C. S. Chem. Comm., pp. 885–886, (1976).
Ishikawa et al., J. Fluorine Chem., 22:585, (1983).
Hemer et al., J. Fluorine Chem., 29:86, (1985).

*Primary Examiner*—Nicky Chan
*Attorney, Agent, or Firm*—Irving M. Fishman; Luther A. R. Hall

[57] ABSTRACT

Zinc compounds of formula II $$CF_3CCl_2ZnCl.yL \quad (II)$$

wherein y is 1 or 2 and L is a solvent ligand selected from the group of the N-disubstituted acid amides, N-substituted lactams and the organic sulfoxides, are suitable for reaction with $CO_2$, COS or $SO_2$ to give, after working up, the acids of formula I $$CF_3CCl_2-X \quad (I)$$

wherein X is —$CO_2H$, —CSOH or —$SO_2H$, in good yield.

10 Claims, No Drawings

PROCESS FOR THE PREPARATION OF TRIFLUORODICHLOROETHYL-SUBSTITUTED ACIDS AND ZINC COMPOUNDS

The present invention relates to a process for the preparation of 2,2,2-trifluoro-1,1-dichloroethylcarboxylic, -thiocarboxylic and -sulfinic acid using adducts of 2,2,2-trifluoro-1,1-dichlorozinc chloride with a solvent and to said adducts.

Adducts of 2,2,2-trifluoro-1,1-dichloroethyl zinc chloride with ethers, e.g. dioxane and tetrahydrofuran, are known from U.S. Pat. No. 3,290,333. In Collection Czechoslov. Chem. Commun., Vol. 37, pp. 3946–3349 (1972), A. Posta and O. Paleta teach that the reaction of an adduct of 2,2,2-trifluoro-1,1-dichlorozinc chloride and dioxane with an acetyl chloride, in contrast to the same reaction with a perfluoroalkyl zinc chloride, does not yield the expected ketone. Our own investigations showed that the described zinc chloride adducts are also unable to react with carbon dioxide. This result is confirmed in J.C.S. Chem. Comm., pp. 885–886 (1976), where it is shown that not even perfluoroalkyl zinc iodides react with carbon dioxide. J. Fluorine Chemistry 22, p. 585, (1983) teaches that perfluoroalkyl iodides are reacted with $CO_2$, in the presence of zinc and dimethylformamide as solvent, to perfluoroalkylcarboxylic acids when the reaction is carried out under ultrasonic irradiation.

It is an object of the present invention to provide a process for the preparation of trifluorodichloroethyl-substituted acids of formula I $$F_3C-CCl_2-X \qquad (I)$$

wherein X is —COOH, —C(S)OH or —$SO_2$H, by reacting an organometal compound with $CO_2$, COS or $SO_2$, in the presence of an inert solvent, and subsequent hydrolysis, which process comprises using a zinc compound of formula II $$CF_3CCl_2ZnCl.yL \qquad (II)$$

as organometal compound, wherein y is 1 or 2 and L is a solvent ligand selected from the group of the N-disubstituted acid amides, N-substituted lactams and organic sulfoxides.

It is preferred to use $SO_2$ and, most particularly, $CO_2$, in the process of this invention for the preparation of 2,2,2-trifluoro-1,1-dichlorosulfinic acid and 2,2,2-trifluoro-1,1-dichloropropionic acid.

The zinc compounds of formula II are novel and also constitute an object of the present invention.

In formula II, L as an N-disubstituted acid amide is preferably a carboxamide, in particular one of the formula

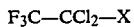

wherein $R^1$ is a hydrogen atom, alkyl of 1 to 12, preferably 1 to 4, carbon atoms, which is unsubstituted or substituted by halogen, preferably by fluorine or chlorine, or is cycloalkyl containing 4 to 7 ring carbon atoms which is unsubstituted or substituted by $C_1$–$C_4$alkyl or halogen, or is alkenyl of 2 to 12, preferably 2 to 4, carbon atoms, phenyl, benzyl or —$NR^2R^3$, where $R^2$ and $R^3$ are each independently of the other $C_1$–$C_{12}$alkyl, cycloalkyl containing 5 or 6 ring carbon atoms, or $R^2$ and $R^3$, when taken together, are tetramethylene or pentamethylene, each of which may be interrupted by —O—, —S— or —$NR^4$ ($R^4$=$C_1$–$C_4$alkyl).

$R^1$ is preferably a hydrogen atom or methyl. $R^2$ and $R^3$ are preferably methyl or ethyl.

Examples of acid amides are dimethylformamide, diethylformamide, dimethylacetamide, tetramethylurea and N-formylpyrrolidine. Dimethylformamide is particularly preferred.

L as N-substituted lactam preferably has the formula

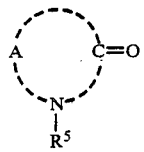

wherein A is dimethylene, trimethylene, tetramethylene or pentamethylene, and $R^5$ is $C_1$–$C_{12}$alkyl, preferably $C_1$–$C_4$alkyl, cyclohexyl or cyclopentyl. $R^5$ is preferably methyl or ethyl. Examples of such lactams are N-methylpropiolactam, N-methylpyrrolidone, N-ethylpyrrolidone, N-methylpiperidinone, N-methyl-ϵ-caprolactam, with N-methylpyrrolidone being preferred.

L as an organic sulfoxide corresponds preferably to the formula

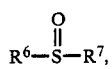

wherein each of $R^6$ and $R^7$ independently of the other is $C_1$–$C_{12}$alkyl, preferably $C_1$–$C_4$alkyl, or $R^6$ and $R^7$, when taken together, are tetramethylene or pentamethylene. Examples of organic sulfoxides are: dimethyl sulfoxide, methylethyl sulfoxide, diethyl sulfoxide, tetramethylene sulfoxide and pentamethylene sulfoxide.

Preferred zinc compounds of formula II are those in which L is an N-disubstituted carboxamide. In formula II, y is preferably 2. A particularly preferred zinc compound is $CF_3CCl_2ZnCl.2$ dimethylformamide.

The zinc compounds of formula II are prepared in a manner known per se by the direct reaction of zinc, preferably in the form of zinc dust, with 1,1,1-trifluoro-2,2,2-trichloroethane excluding air and moisture and in an inert solvent. It is advantageous to cool the reaction mixture. The zinc compounds of this invention can then be isolated in conventional manner by removing the solvent or by crystallisation.

Another preparatory method comprises dissolving the known ether adducts of $CF_3CCl_2ZnCl$ (q.v. U.S. Pat. No. 3,290,333) in a solvent L and heating the solution to about 100° C., whereupon the adducts of the invention are formed by ligand exchange and can then be isolated in known manner.

The zinc compounds of this invention are crystalline compounds which are stable when air and moisture are excluded. It is surprising that the zinc compounds of the invention react with $CO_2$, COS and $SO_2$. It is possible, but not necessary, to apply ultrasonic irradiation. The desired acids are formed in good yield and excellent purity. The process is particularly economic owing to the use of inexpensive starting materials.

The process of the invention is preferably carried out in an inert polar aprotic solvent. Illustrative of such solvents are in particular ethers, tertiary amines, sulfones and solvents corresponding to the ligand L. Typical solvents are: dimethyl ether, diethyl ether, dibutyl ether, dioxane, tetrahydrofuran, ethylene glycol dimethyl or diethyl ether, diethylene glycol dimethyl ether, triethylene glycol dimethyl ether, dimethyl sulfone, tetramethylene or pentamethylene sulfone, trimethylamine, triethylamine, methyl diethylamine, tripropylamine, tributylamine, N-methylmorpholine, N-methylpiperidine, N-methylpyrrolidine, pyridine and N-methylpyrrole.

The inert solvent is preferably an N-disubstituted acid amide, an N-substituted lactam or an organic sulfoxide. Most preferably, the ligand and the solvent are identical. The most preferred solvent is dimethylformamide. Another embodiment of the process comprises using zinc compounds of formula II, wherein y is 2 and L is dimethylformamide.

An advantageous embodiment of the process comprises using a solvent corresponding to the ligand L and preparing the zinc compound II in situ by reacting $CF_3CCl_3$ with zinc and then carrying out the reaction with $CO_2$, COS or $SO_2$.

The process of the invention is conveniently carried out in the temperature range from 0° to 50° C., preferably at room temperature. The process can be carried out under normal pressure or under over-pressure, e.g. in an autoclave, and the pressure may be up to about 100 bar, preferably up to 50 bar.

To isolate the acids, the reaction mixture is subjected to hydrolysis. The hydrolysis is conveniently carried out with a dilute mineral acid, e.g. hydrochloric acid or sulfuric acid, which is suitably mixed with ice to cool the reaction mixture. After the hydrolysis, the resultant acids may be extracted with a suitable solvent, e.g. diethyl ether. The solvent is then removed by distillation to yield the desired acids, which may in turn be purified by distillation.

It has proved expedient to isolate the zinc salts which have formed during the reaction before hydrolysing the reaction mixture. The zinc salts are obtained as crystalline solids and can be readily isolated by crystallisation. This is done by removing the solvent and recrystallising the residue from a suitable solvent. The zinc salts may correspond to the formulae $(CF_3CCl_2Y)_2Zn.yL$ or $(CF_3CCl_2Y)ZnCl.yL$ wherein Y is —C(O)O—, —C(S)O— or —S(O)O—. The acids can be obtained from the zinc salts by hydrolysis.

The acids obtained by the process of this invention may be suitably used as esterification catalysts or for the preparation of surface-active compounds, of oil and water repellants and of plant protective agents (q.v. German Offenlegungschrift No. 1 900 758).

The following Examples illustrate the invention in more detail. The reations are carried out with the exclusion of moisture and in an inert gas atmosphere (nitrogen or argon).

EXAMPLE 1

Preparation of $CF_3CCl_2ZnCl$ $(SL)_n$ complexes 65.4 g (1 mole) of zinc dust (activated according to Fieser & Fieser) are suspended in a solvent (SL) in a 1 liter three-necked flask and then 188 g (1 mole) of $CF_3CCl_3$ are slowly added (see Table 1 for amount of solvent, reaction time and reaction temperature). The reaction mass is subsequently filtered at the indicated reaction temperature over "Selecta" filter flakes and the complexes precipitate in crystalline from the cold filtrate or upon cooling the filtrate. When using dimethylformamide (DMF) as solvent, the complexes are precipitated by adding diethyl ether ($Et_2O$). The complexes are further purified by recrystallisation from the respective solvent and, if the solvent employed is dimethylformamide, from $EtO_2$. The solvent is removed by decantation and the colourless crystalline residue is dried in vacuo. The yields are 70–80%. The results are reported in Table 1.

TABLE 1

| Complex | Amount of solvent | Reaction time (hours) | Reaction temperature | melting point (°C.) |
| --- | --- | --- | --- | --- |
| $CF_3CCl_2ZnCl$ (dioxane) | 500 ml | 3 | 101° C. | 173 |
| $CF_3CCl_2ZnCl$ ($Et_2O$) | 800 ml | 20 | room temperature | 105 |
| $CF_3CCl_2ZnCl$ $(THF)_2$* | 800 ml | 3 | room temperature | 135 |
| $CF_3CCl_2ZnCl$ $(DME)_1$** | 800 ml | 3 | room temperature | 68 |
| $CF_3CCl_2ZnCl$ $(DMF)_2$ | 500 ml | 2 | room temperature | 67 |

*tetrahydrofuran,
**dimethoxyethane

EXAMPLE 2

Preparation of $CF_3CCl_2ZnCl$ $(DMF)_2$ by ligand exchange reaction 4.0 g (12 mmols) of of $CF_3CCl_2ZnCl$ ($EtO_2$) are dissolved at room temperature in 50 1 ml of $EtO_2$. With efficient stirring, 2 ml (26 mmols) of dimethylformamide are slowly added and after a time a two-phase system forms, with the DMF complex settling in oily form as lower phase. After a few minutes this complex begins to crystallise. The crystals are isolated by decantation, washed with $EtO_2$ and then dried in vacuo (yield: >95%).

EXAMPLE 3

Preparation of 1,1,1-trifluoro-2,2-dichloropropionic acid by the single vessel process 65.4 g (1 mole) of zinc dust (activated according to Fieser & Fieser) are suspended in 500 ml of dimethylformamide in a three-necked flask and then 188 g (≙120 ml; 1 mole) of $CF_3CCl_3$ which has been freshly dried over a molecular sieve and subsequently distilled are added slowly to this suspension. After a few minutes the zinc begins to dissolve and the reaction mixture exotherms. The reaction temperature is kept below 30° C. by external cooling. The batch is then stirred for 1 hour and filtered over "Selecta" filter flakes (available from Schleicher & Schüll). With efficient stirring, CO₂ gas is bubbled into the clear, reddish brown filtrate over a frit for 6 hours. Initially strong absorption occurs. Then the solution is poured into a mixture of 500 ml of 10% aqueous HCl and 300 g of ice and extracted with 5×300 ml of EtO₂. The combined extracts are washed with 200 ml of 2% aqueous HCl, dried over MgSO₄ and concentrated by rotary evaporation at room temperature. The residual brown liquid is distilled at 26 mbar, the acid being obtained at 62°–64° C. as a colourless liquid (yield: 50%). The pure acid solidifies at room temperature and has a melting point of 25°–30° C.

EXAMPLE 4

Preparation of 1,1,1-trifluoro-2,2-dichloropropionic acid starting from isolated CF₃CCl₂ZnCl(SL)ₙ complexes In a 1 liter three-necked flask, 1 mole of each of the complexes listed in Table 1 is dissolved at room temperature in 500 ml of dimethylformamide and the solution is treated with CO₂ gas and worked up as described in Example 3. The isolated acid is obtained in yields from 35–50%.

EXAMPLE 5

Preparation of (CF₃CCl₂COO)₂Zn(DMF)

In a 90 ml glass autoclave, 35 ml of dimethylformamide (DMF) are added to 16.4 g (50 mmols) of CF₃CCl₂ZnCl(EtO₂) with efficient stirring. Then CO₂ gas is introduced under pressure and the conditions are kept constant for 24 hours at 5.0 bar and 40° C. When the reaction is complete, the solvent is stripped off under high vacuum at room temperature and the yellow resinous residue is digested with ether. The residual solid is recrystallised from acetone, affording 8.2 g (62%) of colourless needles with a melting point of 188° C. Hydrolysis as performed in Example 3 yields the free acid.

EXAMPLE 6

Preparation of CF₃CCl₂SO₂ZnCl(DMF)

The procedure of Example 5 is repeated, introducing SO₂ instead of CO₂ gas and maintaining a pressure of 2.2 bar over 24 hours at 40° C. The solvent is stripped off under reduced pressure and the residual solid is digested with ether, affording 12.2 g (53%) of colourless crystals with a melting point of 100°–110° C. Hydrolysis as performed in Example 3 yields the free sulfinic acid.

What is claimed is:

1. A process for the preparation of a trifluorodichloroethyl-substituted acid of the formula

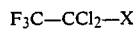

$$F_3C-CCl_2-X \qquad (I)$$

wherein X is —COOH, —C(S)OH or —SO₂H, by reacting an organometal compound with CO₂, COS or SO₂, in the presence of an inert solvent, and subsequent hydrolysis, which process comprises using a zinc compound of formula II

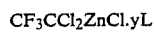

$$CF_3CCl_2ZnCl \cdot yL \qquad (II)$$

as organometal compound, wherein y is 1 or 2 and L is a solvent ligand selected from the group of the N-disubstituted acid amides, N-substituted lactams and organic sulfoxides.

2. A process according to claim 1, wherein the inert solvent is a polar aprotic solvent.

3. A process according to claim 2, wherein the solvent is an N-disubstituted acid amide, an N-substituted lactam or an organic sulfoxide.

4. A process according to claim 1, wherein the solvent ligand L and the inert solvent are identical.

5. A process according to claim 1, wherein y is 2 and L is dimethylformamide.

6. A process according to claim 1, wherein the reaction is carried out in a solvent corresponding to the solvent ligand L and the zinc compound of formula II is prepared in situ by reacting CF₃—CCl₃ with zinc.

7. A process according to claim 1, wherein the reaction is carried out in the temperature range from 0° to 50° C.

8. A process according to claim 1, wherein the hydrolysis of the reaction mixture is carried out with a dilute mineral acid.

9. A process according to claim 1, wherein the reaction is carried out under elevated pressure.

10. The process of claim 1 wherein a zinc salt is formed as an intermediate after said reaction of said organometal compound with CO₂, COS, or SO₂ and said salt is isolated prior to said hydrolysis.

* * * * *